United States Patent [19]

Richmond

[11] 4,399,044

[45] Aug. 16, 1983

[54] TEXTILE SOFTENING COMPOSITION

[75] Inventor: James M. Richmond, Naperville, Ill.

[73] Assignee: Akzona Incorporated, Asheville, N.C.

[21] Appl. No.: 344,685

[22] Filed: Feb. 1, 1982

[51] Int. Cl.³ .................. D06M 13/40; D06M 13/46
[52] U.S. Cl. .................................... 252/8.8; 548/341;
260/462 R; 260/502.3
[58] Field of Search ......................................... 252/8.8

[56] References Cited

U.S. PATENT DOCUMENTS

| | | | |
|---|---|---|---|
| 2,897,170 | 7/1959 | Gruber | 564/196 |
| 3,074,815 | 1/1963 | Lee et al. | 252/8.8 |
| 3,546,115 | 12/1970 | Gill et al. | 252/8.8 |
| 4,320,013 | 3/1982 | Lohman | 252/8.8 |

FOREIGN PATENT DOCUMENTS 2738515  3/1978  Fed. Rep. of Germany ....... 252/8.8

*Primary Examiner*—Maria Parrish Tungol
*Attorney, Agent, or Firm*—Francis W. Young; Daniel N. Christus

[57] ABSTRACT

A composition for imparting softness to textile materials, comprising an ethoxylated amido amine quaternary salt or an ethoxylated imidazolinium quaternary salt.

27 Claims, No Drawings

TEXTILE SOFTENING COMPOSITION

BACKGROUND OF THE INVENTION

This invention relates to textile softening compositions which may be added to the last rinse water after a conventional process so as to impart a more pleasant "feel" to the textiles. The compositions have further advantages in that they provide anti-static properties to the treated textiles and reduce the extent of wrinkling or creasing of fabrics in the wash, and render any wrinkles or creases formed more easily removed by ironing. Furthermore, the compositions have a lubricating effect on the fabrics so as to reduce the friction required to move an iron across the fabric and thereby reduce the effort required for ironing.

There are many known prior art textile softening or antistatic compositions. U.S. Pat. No. 3,567,635, issued to Ballou on Mar. 2, 1971, discloses a cationic quaternary ammonium compound including one amido amine group on the quaternary nitrogen. Anions disclosed are limited to the nitrate anion. Preparation of the compounds is by mixing in specified ratios.

U.S. Pat. Nos. 3,897,348, issued to Atkinson on July 29, 1975, and 3,976,581, issued to Rose on Aug. 24, 1976, disclose a cationic adduct of a substituted ammoniamidate that also includes one amidoamine group on the quaternary nitrogen. Anions disclosed include phosphates, polyphosphates, borates, and citrates. All such adducts must be either aromatically substituted or include a carbon-carbon double bond.

U.S. Pat. No. 3,984,335, issued to Ciko et al. on Oct. 5, 1976, discloses quaternized fatty amides, the compounds including substituents selected from the group consisting of monovalent alkyl radicals and sulfonated monovalent alkyl radicals containing 1-3 carbon atoms. Neither alkoxylated compounds nor boron-containing compounds are disclosed.

SUMMARY OF THE INVENTION

The invention is a composition for imparting softness to textile materials and comprises an ethoxylated amido amine quaternary salt corresponding to the structural formula:

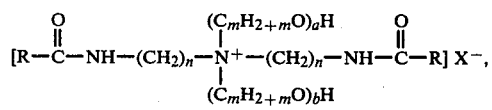

wherein R is selected from the group of hydrocarbon radicals containing from about 6 to about 22 carbon atoms, said radicals being either cyclic or straight- or branched-chain aliphatics, or aromatics, a and b are integers whose sum is between 2 and 20, m is an integer between 2 and 4, n is an integer between 2 and 6, and X is a boron-containing anion. An alternate embodiment of the invention comprises a composition for imparting softness to textile materials including an ethoxylated imidazolinium quaternary salt corresponding to the formula

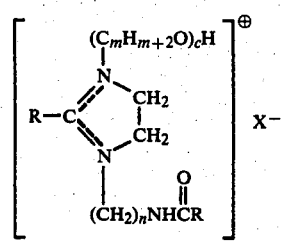

wherein R, m, n, and X are as stated hereinabove, and wherein c is an integer between 1 and 10. The above formula for the imidazolinium quaternary salt is a shorthand representation for the more accurate structural representation,

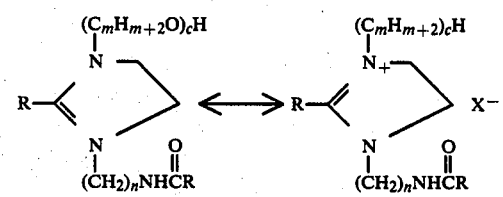

A further aspect of the invention comprises compounds where the anion is selected from the organoborate group including:

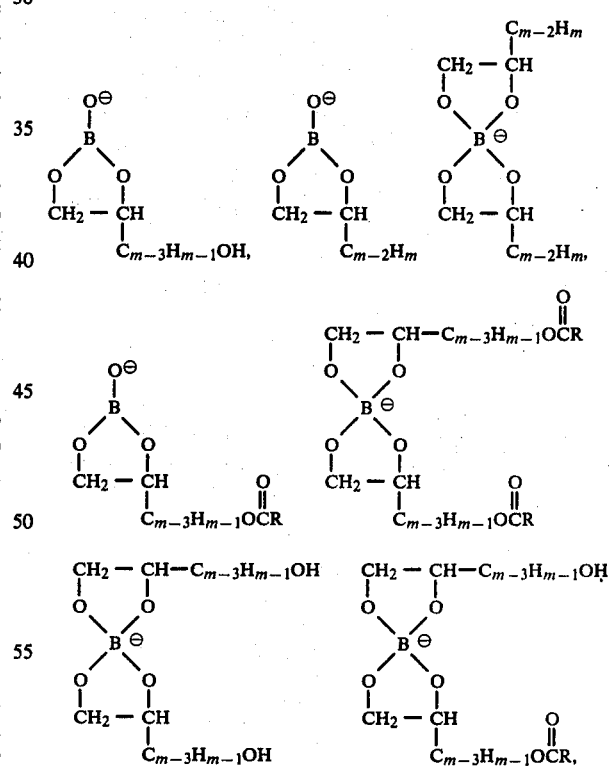

wherein m is as defined above, for reactions including triglycerides combined with triamines, boric acid, and alkylene oxides.

Yet another aspect of the present invention may comprise a formulation wherein R is the heptadecanyl radical. A still further aspect of the present invention may comprise a formulation wherein X is the dihydroborate anion $H_2BO_3^-$.

The present preferred compositions in their pure forms are liquids at room temperature. Thus, they may frequently be transported in tankwagons or in railroad tank cars without the necessity for steam heating to maintain them in a liquid state. Commercial users of full strength compositions will not need to melt them so as to permit their use in water-textile softener solutions. Other advantages of the invention will become apparent in the remainder of the specification.

DESCRIPTION OF THE PREFERRED EMBODIMENTS

The textile softening compositions of the present invention can be conveniently prepared, for example, by the addition of diethylene triamine to a long-chain saturated fatty acid of the formula

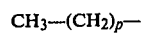

and by then reacting the above mixture with ethylene oxide and an anion-containing agent. A "long-chain saturated fatty acid" is a compound of the general formula above, wherein R is an alkyl radical of the general formula:

$$CH_3-(CH_2)_p-$$

and wherein b is an integer having a value of 14, 15, or 16.

The anion X in the compositions of the present invention is preferably the dihydroborate anion, $H_2BO_3^-$, and may be formed in the composition from the presence of boric acid, $H_3BO_3$, "Borax," $Na_2B_4O_7 \cdot XH_2O$, or partially or completely hydrolyzed organoborate esters such as trimethylborate.

Finally, the composition is ethoxylated with ethylene oxide under heat and pressure. The ethylene oxide is digested for several hours so as to ensure complete reaction.

Another example of a method by which the present textile softening compositions may be prepared is by the addition of diethylene triamine to a triglyceride derived from tallow, white grease, yellow grease, coconut oil, palm kernel oil, canola oil, fish oils, or other naturally derived triglycerides of the formula,

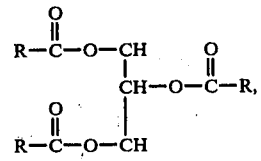

wherein R is as defined hereinabove. The yield is a reaction mixture which includes amidoamidates of the formula

monoglycerides and diglycerides of the formulae

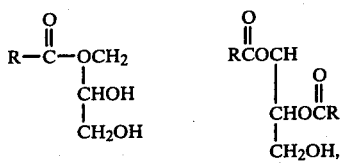

and glycerine

in amounts varying depending upon the mole ratio of the reactants triglyceride and diethylene triamine.

Without further purification, this reaction mixture is combined with boric acid, $H_3BO_3$, and alkylene oxides such as ethylene oxide, propylene oxide, or butylene oxide and heated under pressure to yield ethoxylated amidoamine quaternary ammonium salts corresponding to the structural formula:

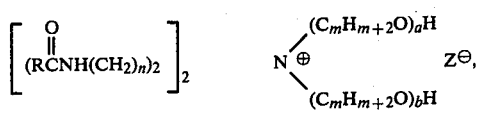

wherein Z denotes that the anion of the above ethoxylated amidoamine quaternary ammonium salt can be any two or more of the anions included in the group of anions comprising X. Each molecule of the above salt may have only one of the anions from the group X. A batch of the salt will, of course, contain many molecules and therefore many of the anions from the group X.

As yet another example of a method by which the present textile softening compositions may be prepared, diethylene triamine is added to one of the naturally derived triglycerides as set forth in the previous example. The reaction mixture is heated with vacuum or under azeotropic conditions to remove the water of condensation and yield an imidazoline corresponding to the formula

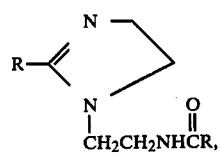

and monoglycerides, diglycerides, and glycerin, the amounts varying depending upon the mole ratio of the reactant triglyceride to diethylene triamine. This reaction mixture, without further purification or separation, is combined with boric acid ($H_3BO_3$) and alkylene oxides such as ethylene oxide, propylene oxide, and butylene oxide and heated under pressure to yield the ethoxylated imidazolinium quaternary ammonium salt corresponding to the formulae represented by the resonance structure:

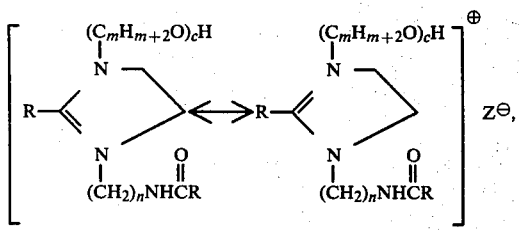

wherein Z, C, R, n, and m are as set forth hereinabove.

It should be apparent that diethylene triamine can be replaced with a like molar amount of triethylene tetraamine or tetraethylene pentaamine in the examples above yielding diimidazolinium quaternary ammonium salts or amidoamine quaternary ammonium salts having multiple quaternary ammonium functionality.

Solvents such as alcohols, glycols, esters, or mineral spirits may be used in any of the above reactions but are unnecessary.

The invention may be illustrated by the following specific examples.

EXAMPLE 1

To a one-liter, three-neck round bottom flask fitted with a mechanical stirrer, Dean-Stark trap and condenser, and automatic temperature control is added 402.5 grams (1.48 gram moles) of Neofat ® 18-55, a triple pressed stearic acid manufactured by the Armak Company, 300 South Wacker Drive, Chicago, Ill. 60606. The Neofat ® 18-55, having a melting point of approximately 69° C., is heated to 120° C. Upon the addition of 76.5 grams (0.741 gram moles) of diethylene triamine to the melted Neofat ® 18-55, the temperature of the mixture increases to 150° C. The temperature of the mixture drops quickly to and is maintained with additional heat at 140° C. as water is removed from the mixture via the Dean-Stark trap. After six hours, 20 milliliters (1.11 gram moles) of water had been collected. The theoretical neutralization equivalent was 610; an actual value of 599 was determined by titration. The reaction mixture is cooled, and has as its major component an intermediate, the bis stearyl amide of diethylene triamine:

166.7 grams (0.26 gram moles) of this intermediate is transferred to a one-liter, stirred autoclave and blended with 20.1 grams (0.326 gram moles) of boric acid, 20.2 grams (0.326 gram moles) of ethylene glycol, and 56.3 grams (0.95 gram moles) of isopropyl alcohol. The autoclave is sealed, and the mixture heated to 85° C., purged twice with 30 pounds/in² gauge (psig) nitrogen, and vented to 8 psig. 49.7 grams (1.17 gram moles) of ethylene oxide is added to the autoclave at 47 psig, and the mixture allowed to digest for three hours. Titration of the mixture with standard hydrochloric acid and sodium tetraphenyl borate indicated 0.88 and 0.53 milliequivalents per gram, respectively. Further analysis indicated that no amine salt, 0.35 milliequivalents per gram or 23% free amine, and 0.53 milliequivalents per gram or 40% of ethoxylated amido amine quaternary salt were present. The quaternary borate is believed to have the following formula:

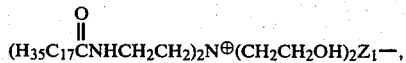

wherein $Z_1$, is selected from the group $H_2BO_3{-}$ and

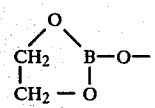

EXAMPLE 2

A two-liter, three-neck round bottom flask fitted with a mechanical stirrer, automatic temperature controller, Dean-Stark trap, and condenser was charged with 401.3 grams (1.49 gram moles) of Neofat ® 18-55 (triple pressed stearic acid), 257 milliliters of xylene, and 77.0 (0.746 gram mole) of diethylene triamine, and the mixture heated to reflux (135°-157° C.). The theoretical water loss is 40 ml (2.22 gram moles); during a four-hour period, 37 milliliters (2.05 gram moles) is collected. The major intermediate product formed in this reaction after distillation of xylenes had a neutralization equivalent of 594, and was believed to have the imidazoline structure:

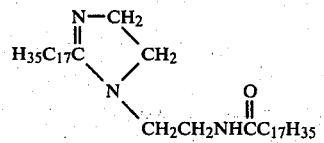

204.5 grams (0.344 gram moles) of this imidazoline, 26.6 grams (0.430 gram moles) of boric acid, 26.7 grams (0.430 gram moles) of ethylene glycol, and 27.3 grams (0.455 gram moles) of isopropyl alcohol were added to a one-liter autoclave, which was sealed, heated to 75° C., purged once with 45 psig nitrogen, and vented to 8 psig. The mixture was heated to 90° C., 61.2 grams (1.39 gram moles) ethylene oxide was added under 45 psig, and digested by the mixture over the next five hours. Standard base titration showed no amine salt present; titration with standard hydrochloric acid indicated 0.96 milliequivalents per gram. Further analysis indicated that the final reaction mixture contained 0.36 milliequivalents per gram or 21% unquaterized free amine, and 0.60 milliequivalents per gram or 42% of ethoxylated imidazolinium quaternary salt of the formula represented by the resonance structure:

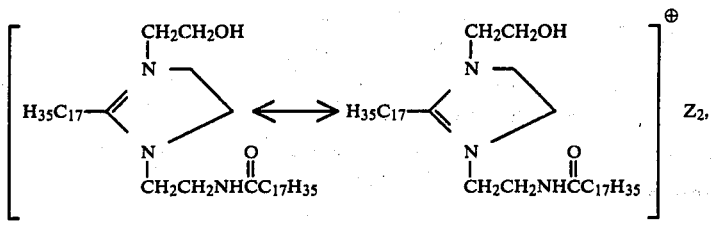

wherein $Z_2$ is selected from the group including $H_2BO_3-$ and

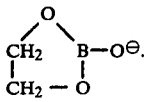

EXAMPLE 3

A two-liter, three-neck, round-bottom flask fitted with a mechanical stirrer, automatic temperature controller, and heating mantle was charged with 920 grams (1.0 gram mole) of bleachable fancy tallow (BFT), 103 grams (1.0 gram mole) of diethylene triamine, and 10 grams (0.05 gram mole) of para-toluene sulfonic acid. This mixture was heated to 150° C. for six hours and analyzed. The theoretical neutralization equivalent was 968; an actual value of 955 was determined by titration. This reaction mixture, composed of the bis-tallow amide of diethylene triamine

and tallow monoglyceride,

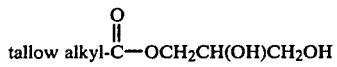

was cooled and transferred to a two-liter, stirred autoclave, where 777 grams (1.25 gram mole) of ethylene glycol, 77.25 grams (1.25 gram mole) of boric acid, and 59 grams (1.0 gram mole) of isopropyl alcohol were blended in. The autoclave was sealed, heated to 85° C., and 220 grams (4.0 gram mole) of ethylene oxide added. This reaction mixture was allowed to react until the ethylene oxide had been consumed as indicated by the reaction pressure. Titration of the reacted mixture with standard hydrochloric acid and sodium tetraphenyl borate gave 0.67 and 0.56 milliequivalents per gram, respectively. Base titration of a sample of the reaction mixture showed no amine salt present. These analyses indicated the presence of 7.5% free amine, nil amine salt, and 46.7% of the quaternary ammonium salt believed to have the structure:

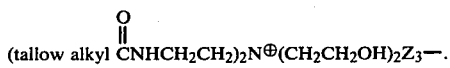

$Z_3-$ may comprise dihydrogen borate, $H_2BO_3-$, and moities of the following type:

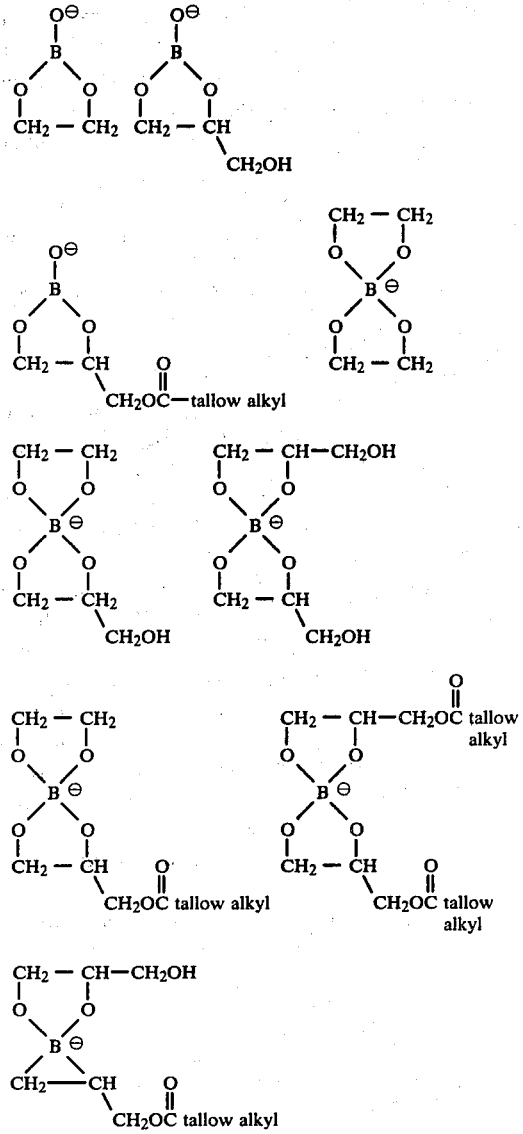

The compounds were evaluated for effectiveness as fabric softeners. Terry towels were washed in commercial washers and in water containing one of three softeners on an equal solids concentration basis: the ethoxylated amido amine quaternary salt of Example 1, the ethoxylated imidazolinium quaternary salt of Example 2, or the widely used, solid, industrial fabric softener, Varisoft 222. The towels were washed once in the machines, and then tested for softness by a panel. The towels were then washed four more times in the machines, and again judged by the panel for softness; no additional fabric softener was used in these last four cycles. If a panel member chose a particular towel as being the softest of the three, the corresponding fabric softener was given 1 point. No points were awarded for the two towels not deemed by each of the thirty panel members to be the softest.

Rewet or wicking is a measure of the absorbency of a fabric. Fabric softeners undesirably lower the absorbency of fabrics; in some cases, repeated treatment of a cotton swatch with a softener can render it nearly waterproof. Rewet is a measure of the height water will climb in a fabric strip suspended vertically over and with one of its ends in a container of water. The higher the rewet, the more absorbent the fabric.

The panel judged the softness as follows:

|  | 1 Cycle | 5 Cycle | Rewet, cm |
|---|---|---|---|
| Example 1 | 33 | 29 | 5.5 |
| Varisoft 222 | 27 | 31 | 5.8 |
| Control (untreated) | 0 | 0 | 19.2 |
| Example 2 | 30 | 28 | 5.2 |
| Varisoft 222 | 29 | 32 | 5.8 |
| Control (untreated) | 1 | 0 | 19.2 |

The results set forth in the above table clearly demonstrate that the novel compounds are comparable in softening performance and rewet to the widely used commercial softener. Further, they are advantageous in that they are liquid at room temperature and below, so that melting is not required before use.

Antistatic properties of towels treated with the softeners of Examples 1 and 2 were, respectively, comparable to and slightly inferior to the antistatic properties of towels treated with Varisoft 222. Antistatic properties of towels treated with either Example 1 or Example 2 softeners were considerably better than antistatic properties of the towels washed in only water (control).

What is claimed is:

1. An aqueous composition for imparting softness to textile materials, said composition comprising an ethoxylated amido amine quaternary salt corresponding to the following structural formula:

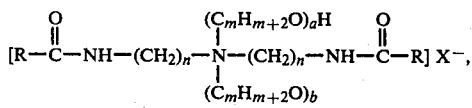

wherein R is selected from the group of hydrocarbon radicals containing from about 6 to about 22 carbon atoms, said radicals being either cyclic or straight- or branched-chain aliphatics, or aromatics, a and b are integers whose sum is between 2 and 20, inclusive, m is an integer between 2 and 4, inclusive, n is an integer between 2 and 6, inclusive, and X is a dihydroborate or organoborate anion.

2. The composition as set forth in claim 1, wherein X is the dihydrogen borate ion.

3. The composition as set forth in claim 1, wherein n is 2.

4. The composition as set forth in claim 2, wherein n is 2.

5. The composition as set forth in claim 1, wherein n is 3.

6. The composition as set forth in claim 2, wherein n is 3.

7. The composition as set forth in claim 1, wherein R is the tallow alkyl radical.

8. The composition as set forth in claim 2, wherein R is the tallow alkyl radical.

9. The composition as set forth in claim 3, wherein R is the tallow alkyl radical.

10. The composition as set forth in claim 4, wherein R is the tallow alkyl radical.

11. The composition as set forth in claim 1, wherein m is 3.

12. The composition as set forth in claim 1, wherein m is 2.

13. The composition as set forth in claim 2, wherein m is 2.

14. The composition as set forth in claim 3, wherein m is 2.

15. The composition as set forth in claim 4, wherein m is 2.

16. The composition as set forth in claim 7, wherein m is 2.

17. The composition as set forth in claim 10, wherein m is 2.

18. An aqueous composition for imparting softness to textile materials comprising an ethoxylated amide amine quaternary salt corresponding to the formula:

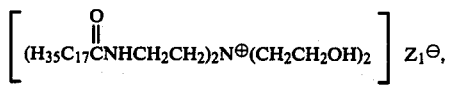

wherein $Z_1$ is selected from the group $H_2BO_3-$ and

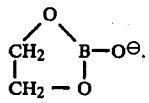

19. The composition as set forth in claim 18, wherein $Z_1$ is selected from the organoborate group:

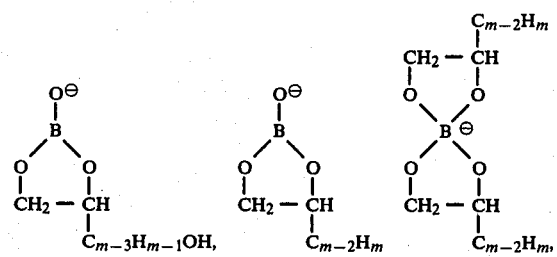

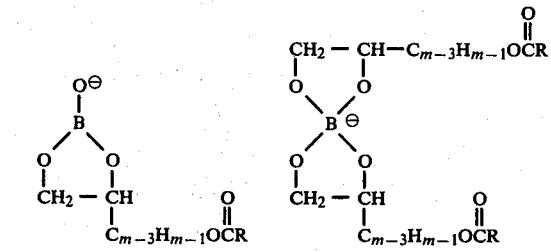

-continued

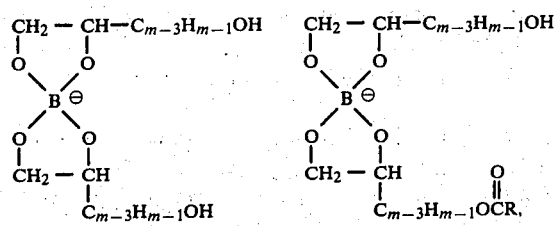

20. An aqueous composition for imparting softness to textile materials and comprising an ethoxylated imidazolinium quaternary salt corresponding to the formula:

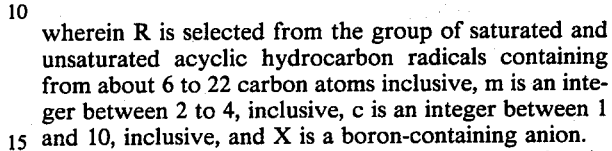

wherein R is selected from the group of saturated and unsaturated acyclic hydrocarbon radicals containing from about 6 to 22 carbon atoms inclusive, m is an integer between 2 to 4, inclusive, c is an integer between 1 and 10, inclusive, and X is a boron-containing anion.

21. The composition as set forth in claim 20, wherein X is dihydrogen borate.

22. The composition as set forth in claim 20, wherein R is the tallow alkyl radical.

23. The composition as set forth in claim 20, wherein m is 2.

24. The composition as set forth in claim 20, wherein m is 3.

25. The composition as set forth in claim 20, wherein c is an integer between 1 and 5, inclusive.

26. The composition as set forth in claim 20, wherein R is the tallow alkyl radical, X is dihydrogen borate, m is 2, and c is 1.

27. The composition as set forth in claim 20, wherein R is the tallow alkyl radical, X is dihydrogen borate, m is 3, and c is 1.

* * * * *